Feb. 22, 1955 PAUL K. FUJIHARA Plant Pat. 1,353
PEACH TREE
Filed Jan. 18, 1954
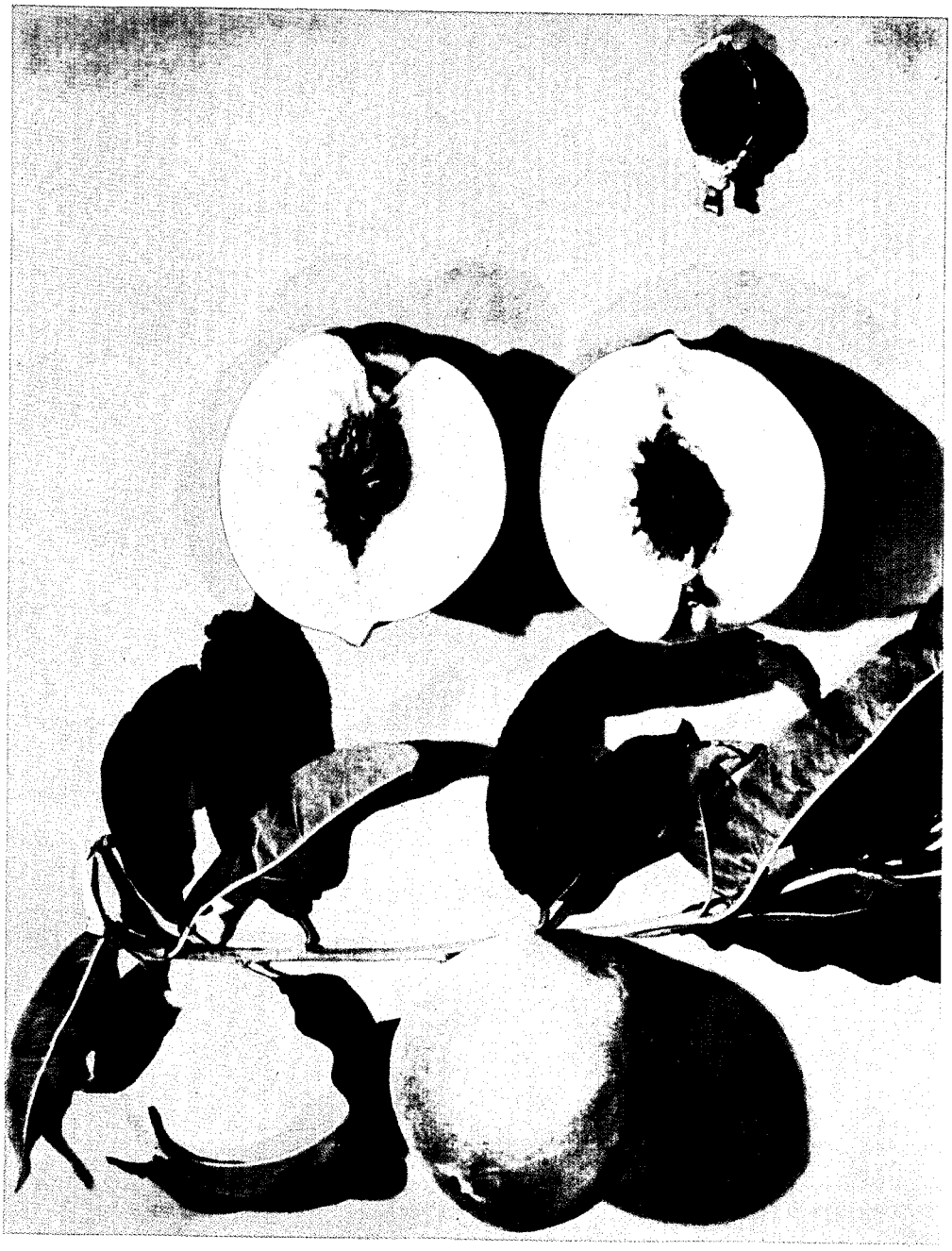
PAUL K. FUJIHARA
INVENTOR
HUEBNER, BEEHLER, WORREL & HERZIG
ATTORNEYS
BY Richard M. Worrel United States Patent Office Plant Pat. 1,353

Patented Feb. 22, 1955

1,353

PEACH TREE

Paul K. Fujihara, Del Rey, Calif.

Application January 18, 1954, Serial No. 404,823

1 Claim. (Cl. 47—62)

The present invention relates to a plant invention or discovery and more particularly to a new and improved variety of peach tree of the freestone type.

The peach tree has certain characteristics in common with the well known but unpatented Babcock, the July Elberta of the Burbank Plant Patent No. 15, the Markham of Plant Patent No. 7, the Ramsey et al. of Plant Patent No. 51, the Stribling of Plant Patent No. 1,144, and the Swim of Plant Patent No. 1,150, with which it will subsequently be compared in greater particularity for descriptive convenience.

The peach tree shown and described was originated and successfully asexually propagated by the applicant on his growing plot near the city of Del Rey in the county of Fresno and State of California. In order to develop a new and improved variety of peach tree, the applicant cross-pollinated a July Elberta with a Babcock which he found blooming at overlapping periods and available for the purpose. In making the cross pollinization the July Elberta was utilized as the male and the Babcock as the female. Pits were removed from fruit which developed from the cross-pollinization and germinated. The characteristics of the resultant seedlings were observed and scions of the seedlings were budded into Kim Elberta peach trees (unpatented) and various unnamed peach seedlings. The budding operations were effected with almost uniform ease and success and the new variety was found to retain its characteristics when so asexually reproduced.

The peach tree of the present invention is most nearly similar to its parent the Babcock but appears to be somewhat more vigorous in growth, generally produces larger fruit when grown under similar conditions which tend to be somewhat rounder, more intense in skin coloring, of a higher sugar content and more intense flavor. It is generally firmer than the Babcock and has superior handling and shipping qualities. Although it blossoms about the same time as the Babcock and over a period of approximately one month, the blossoms are noticeably darker red in color, approximating in color and form those of the July Elberta which blooms a week or ten days later. Fruit of the subject peach tree ripens approximately midway between the ripening of the Babcock and the unpatented common or standard Elberta, approximately twelve to fourteen days later than the Babcock and a week or ten days earlier than the standard Elberta.

As previously referred to, the subject peach tree bears similarity to its parent, the July Elberta. The tree grows vigorously, producing fruit, foliage and new growth abundantly. Like its paternal parents, it is apparently tolerant to many types of soils and it is expected, although not determined at this time, to a wide range of climates. The wood of the tree is quite hardy, being appreciably resistant to winter freezes and late spring frosts. The buds and blossoms are affected by relatively low temperatures. For example, a light freeze late in the spring of 1953 seriously damaged the peach crop in the San Joaquin Valley of California. Although the earlier blossoms of the subject peach tree were somewhat damaged by the frost, the later blossoms resulted in an approximately normal crop of fruit. The tree is of such a character that it may be economically cared for and caused to produce fruit of high quality.

Referring more specifically to the known peach varieties designated above, the subject peach is quite similar to that of Plant Patent No. 15 but is readily distinguished therefrom by a lighter flesh, a somewhat more uniform and more richly colored skin, by an earlier blooming period, and by the production of marketable fruit from a week to ten days earlier than the Burbank or July Elberta peach.

The color of the skin of the subject peach is more closely similar to that of the Markham peach of Plant Patent No. 7 although of greater uniformity in coloring. The flesh is much lighter in color and appreciably less fibrous than the Markham peach. The peach has somewhat more fuzz than the peach of Ramsey et al., Plant Patent No. 51, but in coloring of the skin bears noticeable similarity thereto. The flesh is not nearly as yellow as that of the Ramsey peach but possesses the vigorous growing habits and good shipping qualities of the Ramsey. The almost spherical shape of the fruit of the subject peach tree can be compared with that of the Stribling peach tree of Plant Patent No. 1,144 but is distinguished from the Stribling peach in many characteristics including lighter colored flesh, a later ripening period, and firmer flesh. The fruit of the subject peach tree ripens slightly earlier than that of the Swim peach of Plant Patent No. 1,150, has more uniform skin coloring, somewhat lighter flesh, darker pit and pit well and other distinguishing characteristics. The distinctive pomological characteristics of the peach tree will be apparent by reference to the accompanying drawing, showing a branch of the tree bearing leaves and a whole fruit, a halved fruit illustrating flesh color characteristics, and a pit and by reference to the following description of the peach tree which describes characteristics of the tree when grown under the ecological conditions found in the San Joaquin Valley of the State of California.

The color terminology employed is in accordance with Ridgway's "Color Standards and Color Nomenclature."

Tree: Similar to July Elberta being medium to large, vigorous, round topped, somewhat vase shaped, productive and a regular bearer.

*Trunk and limbs.*—Similar to Kim Elberta, being of medium caliber in relation to length, medium surface roughness, usually somewhat lighter in color than Kim Elberta approximating Argus Brown Plate III with the limbs usually being upright, approaching the vertical. The branches are medium slender and mostly smooth also being somewhat lighter in color than the Kim Elberta.

*Leaves.*—Size.—Widely varying but usually large approximating 6 inches in length by 1⅜ inches in width.

Shape—Tend to curl like Babcock. Acuminate and lanceolate. Marginally minutely serrated.

Color—Upper surface not as dark as leaves of the Kim Elberta approximating Varley's Green of Plate XVIII with the underside of the leaf being somewhat lighter than the upper surface and slightly more yellow as is usual in peach leaves.

Glandular characteristics—Reniform, one or two on each side of petiole, usually alternate but occasionally opposite, lighter green than leaves.

Petiole—length approximately ⅜ to ½ inch, thickness 1/16 inch of characteristic peach channel form on upper side.

*Buds.*—Large to medium size, characteristic Elberta, conic pointed shape and pubescent.

*Blossoms.*—Blooming period extensive and concurrent with Babcock, blossoms remaining on tree for approximately three to four weeks, large like Babcock but more colorful than Babcock, having petals with white tips and shrimp pink inner ends of Plate I.

*Fruit*:

*Maturity.*—Eating ripe date about July 10, twelve to fourteen days later than Babcock and one week to ten days earlier than the standard Elberta.

*Size.*—Usually uniform, large size. Axial diameter 3⅜ inches, transverse diameter in suture plane 3¼ inches and transverse diameter in plane normal to suture plane 3¾ inches.

*Form.*—Only slightly variable and substantially symmetrical, large cheeked, suture relatively shallow but distinct on dorsal side extending from base to apex and slightly depressed adjacent to pistil point, suture visible on ventral side but indistinct.

Stem cavity—ovate, being elongated and broadened in suture plane with suture showing distinctly on dorsal side length 1 to 1½ inches, depth ½ to ¾ inch and width ¾ to 1 inch. Base rounded and blended with stem cavity.

Apex—short with depressions adjacent to pistil point in suture plane. Pistil point short and apical.

Stem—medium size approximating ⅛ to 3/16 inch in diameter.

*Skin.*—Medium to thin, tender, free when fruit is fully ripe, no tendency to crack noticed, scant pubescence.

*Color.*—Skin—predominately Nopal Red under 3 (orange red) of Plate I shading to Barium Yellow of Plate XVI under Column 23 (yellow) or Naphthalene Yellow. Flesh—Ivory Yellow under Column 21 (orange-yellow yellow) Plate XXX, streaked outwardly from the pit well with shades of scarlet red or Spectrum Red of Column 1 (red) or Column 3 (orange red) of Plate I. Surface of pit cavity—Dark Scarlet Red in grooves graduated to pale Scarlet Red on ridges.

*Amygdalin.*—None observed.

*Juice.*—Abundant.

*Texture.*—Varies from firm to medium during ripening progressing from crisp to melting.

*Fibers.*—Minor and tender.

*Ripens.*—Individual fruit ripen substantially evenly but the various fruit on a single tree ripen unevenly so that fruit on a given tree progressively reach maturity over a considerable period.

*Flavor.*—Low acid, somewhat similar to Babcock but sweeter and more intense. Excellent eating quality.

*Aroma.*—Pronounced.

*Stone.*—Free, adhering to flesh only slightly along ventral edge.

Fibers—not pronounced. Few adhering in furrows of pits.

Size—small to medium. Length, approximately 1½ inches, width approximately 1 inch, and thickness ⅞ inch.

Form—substantially oval and full near apex, somewhat tapered to base. Base oblique. Apex bears sharpened point continuous with pronounced blade-wing along ventral edge. Sides substantially symmetrical on opposite sides of suture plane of fruit and deeply furrowed, the ridges between the furrows being relatively more rounded toward the base than toward the apex.

Color—varying from Oxblood Red under Column 1 (red) of Plate I or Claret Brown Number 5 Column 00-R of Plate I to Nopal Red under Column 3 (orange red) on Plate I and for most part being quite dark. Traces of Ivory Yellow of Column 21 (orange-yellow yellow) of Plate XXX on blade-wing of pit and at base.

Tendency to split—no such tendency yet noticeable.

*Use.*—Local and long distance markets; fresh, dried, canned, or frozen.

*Keeping quality.*—Good for freestone.

*Shipping quality.*—Good for freestone.

*Resistance to disease.*—Not observed.

Having thus described my discovery, I claim:

A new and distinct variety of peach tree substantially as illustrated and described characterized by the similarity of its freestone fruit to that of the Babcock peach (unpatented), although tending toward a rounder somewhat larger fruit of higher sugar content and more intense skin coloring than the Babcock; by blossoming about the same time as the Babcock but bearing blossoms of darker red color approximating in color and form those of the July Elberta (Plant Patent No. 15); and by the ripening of the fruit approximately mid-way between the ripening of the Babcock and the standard (unpatented) Elberta.

No references cited.